US012653491B2

(12) United States Patent
Go et al.

(10) Patent No.: US 12,653,491 B2
(45) Date of Patent: Jun. 16, 2026

(54) DOPPLER ULTRASOUND DEVICE AND METHOD FOR CARDIAC OUTPUT MEASUREMENT WITH TWO PROBES

(71) Applicant: EDGECARE INC., Seoul (KR)

(72) Inventors: Doo Young Go, Seoul (KR); Il Seob Song, Goyang-si (KR); Jung Jun Kim, Seoul (KR); Yang Mo Yoo, Seoul (KR)

(73) Assignee: EDGECARE INC., Seoul (KR)

( * ) Notice: Subject to any disclaimer, the term of this patent is extended or adjusted under 35 U.S.C. 154(b) by 0 days.

(21) Appl. No.: 19/238,855

(22) Filed: Jun. 16, 2025

(65) Prior Publication Data

US 2026/0114841 A1 Apr. 30, 2026

(30) Foreign Application Priority Data

Oct. 30, 2024 (KR) ........................ 10-2024-0150627

(51) Int. Cl.
*A61B 8/06* (2006.01)
*A61B 8/00* (2006.01)

(52) U.S. Cl.
CPC .............. *A61B 8/065* (2013.01); *A61B 8/488* (2013.01); *A61B 8/5223* (2013.01); *A61B 8/58* (2013.01)

(58) Field of Classification Search
CPC ....... A61B 8/065; A61B 8/488; A61B 8/5223; A61B 8/58
See application file for complete search history.

(56) References Cited

U.S. PATENT DOCUMENTS

2009/0062654 A1* 3/2009 Zhang ................... G01S 7/5205
600/455

FOREIGN PATENT DOCUMENTS

CN 106388862 A * 2/2017 ......... G01S 7/52077
JP 2013-252423 12/2013

* cited by examiner

*Primary Examiner* — Serkan Akar
(74) *Attorney, Agent, or Firm* — LEX IP MEISTER, PLLC

(57) ABSTRACT

According to the cardiac output measurement device according to the present disclosure, it is possible to measure the cardiac output more easily in a non-invasive manner by calculating the cardiac output based on the first ultrasound reception signal and the second ultrasound reception signal received from the first ultrasound probe and the second ultrasound probe that are located in both directions based on the heart.

8 Claims, 5 Drawing Sheets

<u>10</u>

300

SD1

SD2

300

HSD

1

DOPPLER ULTRASOUND DEVICE AND METHOD FOR CARDIAC OUTPUT MEASUREMENT WITH TWO PROBES

BACKGROUND

1. Field

The present disclosure relates to a cardiac output measurement device.

2. Description of Related Art

Currently, invasive methods are mainly used to measure cardiac output, but have risks such as infection. Recently, various studies are being conducted to solve such problems.

RELATED ART DOCUMENT

Patent Document (Korean Patent) No. 10-1306553 (Registration date, Sep. 3, 2013)

SUMMARY

The present disclosure provides a cardiac output measurement device capable of measuring cardiac output more easily in a non-invasive manner by calculating cardiac output based on a first ultrasound reception signal and a second ultrasound reception signal received from a first ultrasound probe and a second ultrasound probe that are located in both directions based on a heart.

According to an embodiment of the present disclosure, a cardiac output measurement device may include a first ultrasound probe, second a ultrasound probe, and a calculation unit. The first ultrasound probe may be arranged in a first direction based on a heart of a human body, transmit a first ultrasound transmission signal to a first region included in the human body, and receive a first ultrasound reception signal reflected from the first region. The second ultrasound probe may be arranged in a second direction opposite to the first direction based on the heart of a human body, transmit a second ultrasound transmission signal to a second region included in the human body, and receive a second ultrasound reception signal reflected from the second region. The calculation unit may calculate a cardiac output based on the first ultrasound reception signal and the second ultrasound reception signal.

The first region may be located in the first direction based on the heart, and the second region may be located in the second direction based on the heart.

The calculation unit may include: a first calculation unit and a second calculation unit. The first calculation unit may calculate a first cardiac output based on the first ultrasound reception signal. The second calculation unit may calculate a second cardiac output based on the second ultrasound reception signal.

The calculation unit may further include a weighting unit. The weighting unit may determine weights applied to the first cardiac output and the second cardiac output.

A first weight applied to the first cardiac output may be smaller than a second weight applied to the second cardiac output.

The calculation unit may further include a correction unit. The correction unit may apply a predetermined correction constant to a summed cardiac output obtained by summing a first weighted cardiac output obtained by applying the first weight to the first cardiac output and a second weighted cardiac output obtained by applying the second weight to the second cardiac output.

The first cardiac output may be generated from a first spectral Doppler generated from the first ultrasound reception signal. The second cardiac output may be generated from a second spectral Doppler generated from the second ultrasound reception signal.

The cardiac output measurement device may further include a synthesis unit. The synthesis unit may synthesize the first spectral Doppler and the second spectral Doppler to provide a synthesis spectral Doppler.

The cardiac output measurement device may further include an estimation unit. The estimation unit may estimate the cardiac output according to the synthesis spectral Doppler.

The cardiac output measurement device may further include a result providing unit. The result providing unit may provide a result signal when the cardiac output is smaller than a predetermined first reference value or greater than a predetermined second reference value.

In addition to the technical problems of the present disclosure described above, other features and advantages of the present disclosure are described below or can be clearly understood by those skilled in the art to which the present disclosure belongs from such description and explanation.

DETAILED DESCRIPTION

Figure 1:
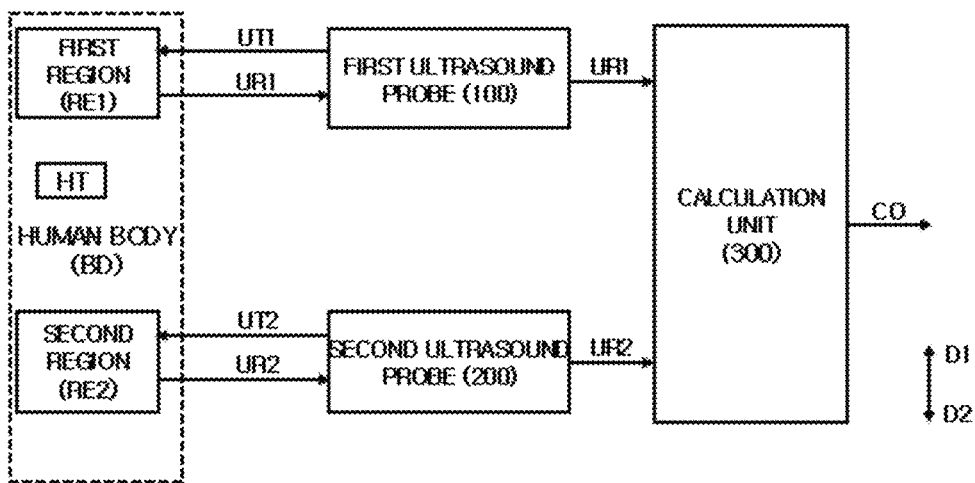
FIG. 1 is a diagram illustrating a cardiac output measurement device according to embodiments of the present disclosure.

In the specification, in adding reference numerals to components throughout the drawings, it is to be noted that like reference numerals designate like components even though components are shown in different drawings.

On the other hand, the meaning of the terms described in the present specification should be understood as follows.

Singular expressions should be understood to include plural expressions unless the context clearly defines otherwise, and the scope of the rights should not be limited by these terms.

It should be understood that the terms 'include' and 'have' do not preclude the existence or addition possibility of one or more other features or numbers, steps, operations, components, parts, or combinations thereof.

Hereinafter, preferred embodiments of the present disclosure designed to solve the above problems will be described in detail with reference to the attached drawings.

Figure 2:
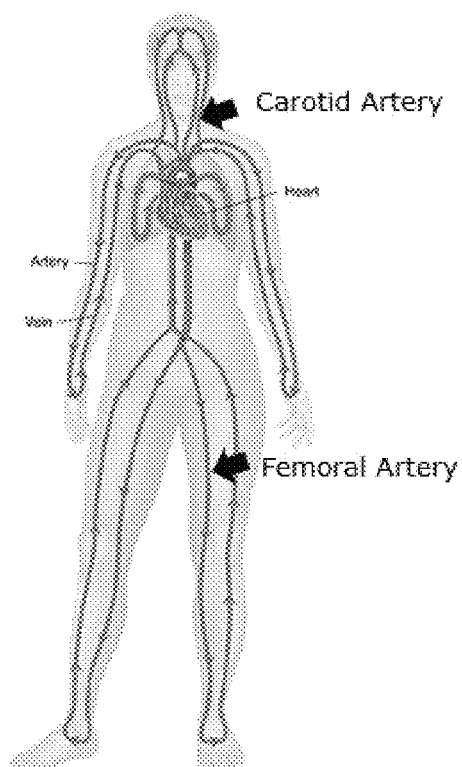
FIG. 2 is a drawing for describing a human body to which the cardiac output measurement device of FIG. 1 is applied.

FIG. 1 is a diagram illustrating a cardiac output measurement device according to embodiments of the present disclosure, and FIG. 2 is a drawing for describing a human body to which the cardiac output measurement device of FIG. 1 is applied.

Referring to FIGS. 1 and 2, a cardiac output measurement device 10 according to an embodiment of the present disclosure may include a first ultrasound probe 100, a second ultrasound probe 200, and an output unit 300.

The first ultrasound probe 100 may be located in a first direction D1 based on a heart HT of a human body BD. For example, the first direction D1 may be a direction toward a head based on the heart HT of the human body BD. The first ultrasound probe 100 may transmit a first ultrasound transmission signal UT1 to a first region RE1 included in the human body BD, and receive a first ultrasound reception signal UR1 reflected from the first region RE1. For example, the first region RE1 may be a region including a carotid artery, and the first ultrasound probe 100 may transmit a first ultrasound transmission signal UT1 to the first region RE1 including the carotid artery, and receive a first ultrasound reception signal UR1 reflected from the carotid artery. Here, a blood vessel included in the first region RE1 is limited to the carotid artery, but the present disclosure is not limited thereto and may be applied to other blood vessels included in the human body BD.

The second ultrasound probe 200 may be located in a second direction D2 opposite to the first direction D1 based on the heart HT of the human body BD. For example, the first direction D1 may be a direction toward legs based on the heart HT of the human body BD. The second ultrasound probe 200 can transmit a second ultrasound transmission signal UT2 to a second region RE2 included in the human body BD and receive a second ultrasound reception signal UR2 reflected from the second region RE2. For example, the second region RE2 may be a region including a femoral artery, and the second ultrasound probe 200 may transmit a second ultrasound transmission signal UT2 to a second region RE2 including the femoral artery and receive a second ultrasound reception signal UR2 reflected from the femoral artery. Here, the blood vessel included in the second region RE2 is limited to the femoral artery, but the present disclosure is not limited thereto and may be applied to other blood vessels included in the human body BD.

In an embodiment, the first region RE1 may be located in the first direction D1 based on the heart HT, and the second region RE2 may be located in the second direction D2 based on the heart HT.

The calculation unit 300 may calculate a cardiac output CO based on the first ultrasound reception signal UR1 and the second ultrasound reception signal UR2. For example, the calculation unit 300 may calculate the cardiac output CO based on the first ultrasound reception signal UR1 reflected from the first region RE1 and the second ultrasound reception signal UR2 reflected from the second region RE2. More specific details will be described later.

The cardiac output measurement device 10 according to the present disclosure may calculate the cardiac output co based on the first ultrasound reception signal UR1 and the second ultrasound reception signal UR2 received from the first ultrasound probe 100 and the second ultrasound probe 200 located in both directions based on the heart HT, thereby measuring the cardiac output CO more easily in the non-invasive manner.

Figure 3:
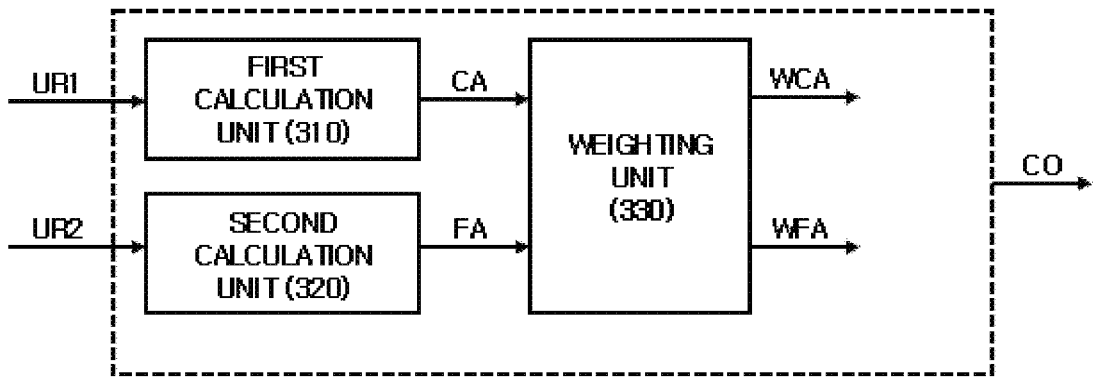
FIG. 3 is a diagram illustrating a calculation unit included in the cardiac output measurement device of FIG. 1.
Figure 4:
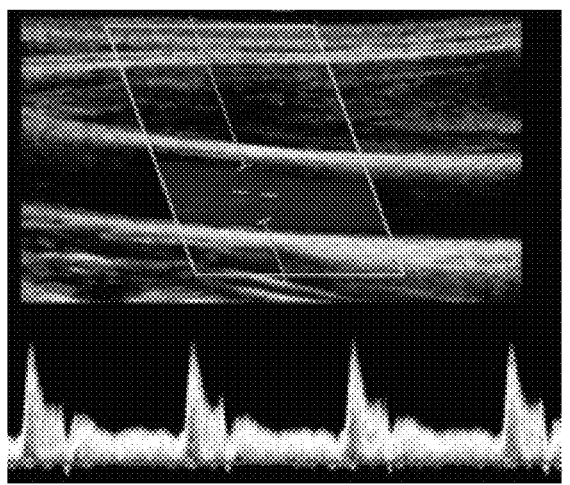
FIGS. 4 and 5 are diagrams for describing an operation of the calculation unit included in the cardiac output measurement device of FIG. 1.
Figure 5:
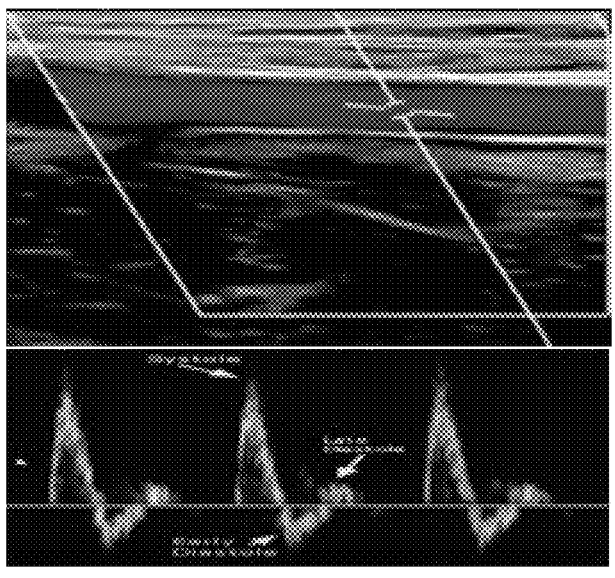
Figure 6:
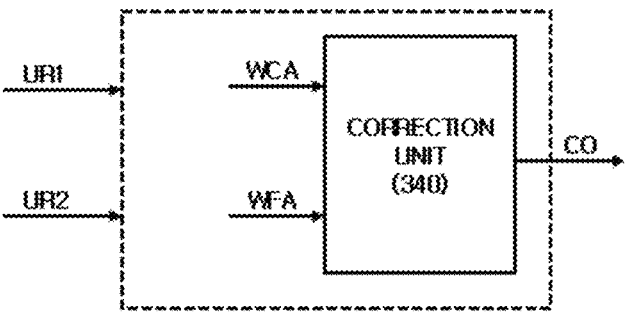
FIG. 6 is a diagram illustrating a correction unit included in the cardiac output measurement device of FIG. 1.

FIG. 3 is a diagram illustrating a calculation unit included in the cardiac output measurement device of FIG. 1, FIGS. 4 and 5 are diagrams for describing an operation of the calculation unit included in the cardiac output measurement device of FIG. 1, and FIG. 6 is a diagram illustrating a correction unit included in the cardiac output measurement device of FIG. 1.

Referring to FIGS. 1 to 6, in an embodiment, the calculation unit 300 may include a first calculation unit 310 and a second calculation unit 320. The first calculation unit 310 may calculate a first cardiac output CA based on the first ultrasound reception signal UR1.

For example, the first cardiac output CA may be determined based on a cross-sectional area of the carotid artery, a velocity-time integral value VTIc for a blood flow of the carotid artery, and a heart rate. The velocity-time integral value VTIc for the blood flow of the carotid artery may mean an integral value over time in a first spectral Doppler SD1, which is a spectral Doppler waveform of the blood flow of the carotid artery.

Here, the first cardiac output CA may be expressed as in [Equation 1] below.

$$CA = Ac * VTIc * HR \qquad \text{[Equation 1]}$$

Here, CA may be the first cardiac output, Ac may be the cross-sectional area of the carotid artery, VTIc may be the velocity-time integral value for the blood flow of the carotid artery, and HR may be the heart rate.

The second calculation unit 320 may calculate a second cardiac output FA based on the second ultrasound reception signal UR2.

For example, the second cardiac output FA may be determined based on a cross-sectional area of the femoral artery, a velocity-time integral value VTIf for a blood flow of the femoral artery, and the heart rate. The velocity-time integral value VTIf for the blood flow of the femoral artery may mean the integral value over time in a second spectral Doppler SD2, which is a spectral Doppler waveform of the blood flow of the femoral artery.

Here, the second cardiac output FA may be expressed as in [Equation 2] below.

$$FA = Af * VTIf * HR \qquad \text{[Equation 2]}$$

Here, CA may be the first cardiac output, Ac may be the cross-sectional area of the femoral artery, VTIf may be the velocity-time integral value for the blood flow of the femoral artery, and HR may be the heart rate.

In an embodiment, the calculation unit 300 may further include a weighting unit 330. The weighting unit 330 may determine weights applied to the first cardiac output CA and the second cardiac output FA. In another embodiment, a first weight applied to the first cardiac output CA may be smaller than a second weight applied to the second cardiac output FA. For example, the first weight applied to the first cardiac output CA may be 0.3, and the second weight applied to the second cardiac output FA may be 0.7.

In an embodiment, the calculation unit 300 may further include a correction unit 340. The correction unit 340 may apply a predetermined correction constant to the summed cardiac output, which is the sum of a first weighted cardiac output WCA in which the first weight is applied to the first cardiac output CA and a second weighted cardiac output WFA in which the second weight is applied to the second cardiac output FA. For example, the correction unit 340 may multiply the first weighted cardiac output WCA and the second weighted cardiac output (WFA) by a predetermined correction constant to calculate the cardiac output.

The cardiac output calculated by the correction unit 340 may be expressed as in [Equation 3] below.

$$CO = \gamma(\alpha CA + \beta FA) \qquad \text{[Equation 3]}$$

Here, CO may be the cardiac output, y may be the correction constant, a may be the first weight, CA may be the first cardiac output, β may be the second weight, FA may be the second cardiac output, the first weighted cardiac output WCA may be a value obtained by multiplying the first weight and the first cardiac output, the second weighted cardiac output WFA may be a value obtained by multiplying the second weight and the second cardiac output, and the summed cardiac output may be a value obtained by summing the first weighted cardiac output WCA and the second weighted cardiac output WFA.

In an embodiment, the first cardiac output CA may be generated from the first spectral Doppler SD1 generated from the first ultrasound reception signal UR1. For example, the first cardiac output CA may be calculated based on the cross-sectional area of the carotid artery, the velocity-time integral value VTIc for the blood flow in the carotid artery, and the heart rate, as in the above [Equation 1].

In addition, the second cardiac output FA may be generated from the second spectral Doppler SD2 generated from the second ultrasound reception signal UR2. For example, the second cardiac output FA may be calculated based on the cross-sectional area of the femoral artery, the velocity-time integral value VTIf for the blood flow in the femoral artery, and the heart rate, as in the above [Equation 2].

Figure 7:
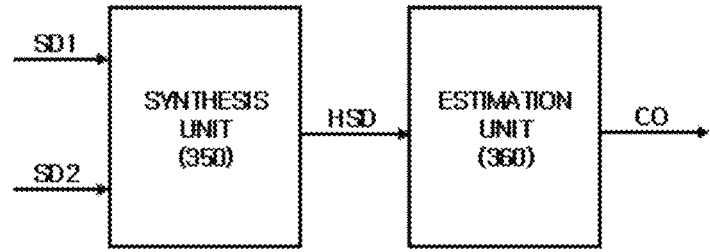
FIGS. 7 and 8 are diagrams for describing a synthesis unit and an estimation unit included in the cardiac output measurement device of FIG. 1.
Figure 8:
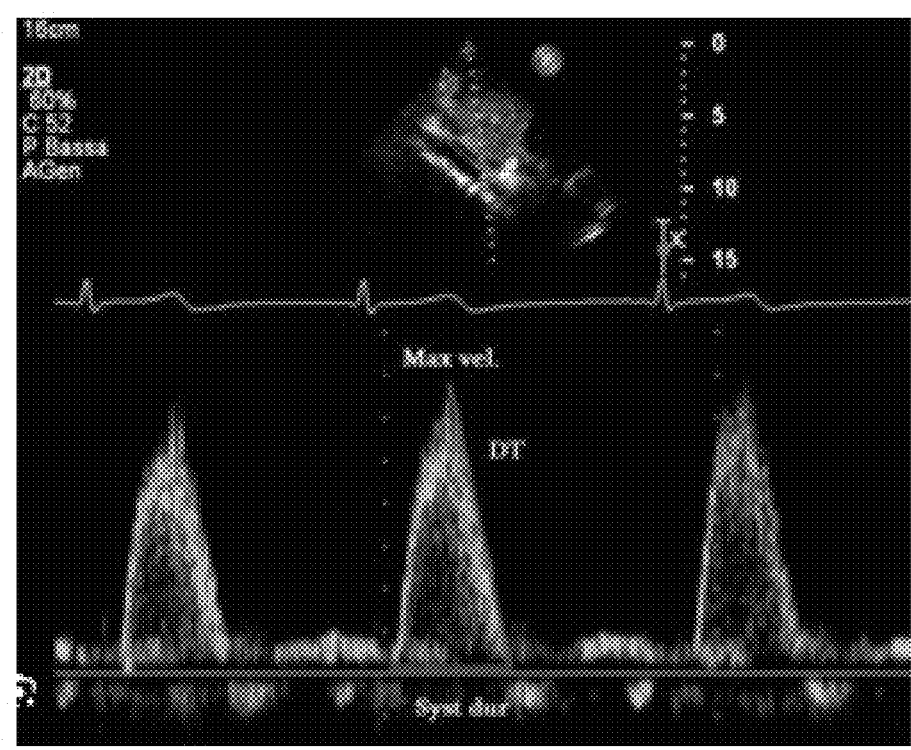
Figure 9:
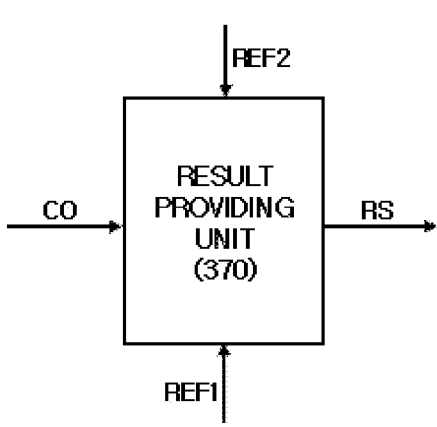
FIG. 9 is a diagram illustrating a result providing unit included in the cardiac output measurement device of FIG. 1.

FIGS. 7 and 8 are diagrams for describing a synthesis unit and an estimation unit included in the cardiac output measurement device of FIG. 1, and FIG. 9 is a diagram illustrating a result providing unit included in the cardiac output measurement device of FIG. 1.

In an embodiment, the cardiac output measurement device 10 may further include a synthesis unit 350. The synthesis unit 350 may synthesize the first spectral Doppler SD1 and the second spectral Doppler SD2 to provide a synthetic spectral Doppler HSD. For example, the synthesis unit 350 may synchronize and synthesize the first spectral Doppler SD1 and the second spectral Doppler SD2 based on peak points to produce the synthetic spectral Doppler HSD.

In an embodiment, the cardiac output measurement device 10 may further include an estimation unit 360. The estimation unit 360 may estimate the cardiac output CO based on the synthetic spectral Doppler HSD. For example, the estimation unit 360 may calculate the velocity-time integral value based on the synthetic spectral Doppler HSD, and may calculate a vascular cross-sectional area by applying a predetermined area weight to the cross-sectional area of the carotid artery and the cross-sectional area of the femoral artery. Thereafter, the estimation unit 360 may calculate the cardiac output CO based on the velocity-time integral value, the vascular cross-sectional area, and the heart rate calculated based on the synthetic spectral Doppler HSD.

In an embodiment, the cardiac output measurement device 10 may further include a result providing unit 370. The result providing unit 370 may provide a result signal RS when the cardiac output CO is smaller than a predetermined first reference value REF1 or greater than a predetermined second reference value REF2. For example, when the cardiac output CO is out of a range determined by the first reference value REF1 and the second reference value REF2, the result signal RS may be provided to provide a notification to the user.

The cardiac output measurement device 10 according to the present disclosure may calculate the cardiac output CO based on the first ultrasound reception signal UR1 and the second ultrasound reception signal UR2 received from the first ultrasound probe 100 and the second ultrasound probe 200 located in both directions based on the heart HT, thereby measuring the cardiac output CO more easily in the non-invasive manner.

According to the present disclosure as described above, the following effects are provided.

According to the cardiac output measurement device according to the present disclosure, it is possible to measure the cardiac output more easily in the non-invasive manner by calculating the cardiac output based on the first ultrasound reception signal and the second ultrasound reception signal received from the first ultrasound probe and the second ultrasound probe that are located in both directions based on the heart.

In addition, other features and advantages of the present disclosure may be newly identified through the embodiments of the present disclosure.

In addition to the technical problems of the present disclosure described above, other features and advantages of the present disclosure are described below or can be clearly understood by those skilled in the art to which the present disclosure belongs from such description and explanation.

What is claimed is:

1. A cardiac output measurement device, comprising:
a first ultrasound probe that is arranged in a first direction based on a heart of a human body, transmits a first ultrasound transmission signal to a first region included in the human body, and receives a first ultrasound reception signal reflected from the first region;
a second ultrasound probe that is arranged in a second direction opposite to the first direction based on the heart of the human body, transmits a second ultrasound transmission signal to a second region included in the human body, and receives a second ultrasound reception signal reflected from the second region; and
a calculation unit that calculates cardiac output based on the first ultrasound reception signal and the second ultrasound reception signal,
wherein the calculation unit further includes a correction unit that applies a predetermined correction constant to a summed cardiac output obtained by summing a first weighted cardiac output obtained by applying the first weight to the first cardiac output and a second weighted cardiac output obtained by applying the second weight to the second cardiac output,
wherein the first cardiac output is generated from a first spectral Doppler generated from the first ultrasound reception signal, and the second cardiac output is generated from a second spectral Doppler generated from the second ultrasound reception signal.

2. The cardiac output measurement device of claim 1, wherein the first region is located in the first direction based on the heart, and the second region is located in the second direction based on the heart.

3. The cardiac output measurement device of claim 2, wherein the calculation unit includes:

a first calculation unit that calculates a first cardiac output based on the first ultrasound reception signal; and a second calculation unit that calculates a second cardiac output based on the second ultrasound reception signal.

4. The cardiac output measurement device of claim 3, wherein the calculation unit further includes a weighting unit that determines weights applied to the first cardiac output and the second cardiac output.

5. The cardiac output measurement device of claim 4, wherein a first weight applied to the first cardiac output is smaller than a second weight applied to the second cardiac output.

6. The cardiac output measurement device of claim 5, further comprising:

a synthesis unit that synthesizes the first spectral Doppler and the second spectral Doppler to provide a synthesis spectral Doppler.

7. The cardiac output measurement device of claim 6, further comprising:

an estimation unit that estimates the cardiac output according to the synthesis spectral Doppler.

8. The cardiac output measurement device of claim 7, further comprising:

a result providing unit that provides a result signal when the cardiac output is smaller than a predetermined first reference value or greater than a predetermined second reference value.

* * * * *